United States Patent [19]

Vágó et al.

[11] Patent Number: 6,075,018
[45] Date of Patent: *Jun. 13, 2000

[54] 1-[2-(SUBSTITUTED VINYL)]-3,4-DIHYDRO-4-DIHYDRO-5+e,UNS H+ee -2,3-BENZODIAZEPINE DERIVATIVES

[75] Inventors: Pál Vágó; József Reiter; István Gyertyán; Gábor Gigler; Ferenc Andrási; Anna Bakonyi; Pál Berzsenyi, all of Budapest; Péter Botka, deceased, late of Budapest, by Hilda Botka, executrix; Erszébet Birkás, Budapest; Tamás Hámori, Budapest; Edit Horváth, Budapest; Katalin Horváth, Budapest; Jenö Körösi, deceased, late of Budapest, by Péter Körösi; Györgyné Máté, Budapest; Imre Moravcsik, Budapest; György Somogyi, Budapest; Eszter Szentkuti, Budapest; Gábor Zólyomi, Budapest, all of Hungary

[73] Assignee: Egis Gyogyszergyar Rt., Budapest, Hungary

[ * ] Notice: This patent is subject to a terminal disclaimer.

[21] Appl. No.: 08/599,235

[22] Filed: Feb. 9, 1996

[30] Foreign Application Priority Data

Feb. 9, 1995 [HU] Hungary .................................. 9500386

[51] Int. Cl.$^7$ ........................ A61K 31/395; C07D 243/02
[52] U.S. Cl. .......................... 514/221; 540/567; 540/557; 514/220
[58] Field of Search ..................... 540/557, 567; 514/220, 221

[56] References Cited

U.S. PATENT DOCUMENTS 4,840,948  6/1989  Lang et al. .............................. 514/221

*Primary Examiner*—John M. Ford
*Attorney, Agent, or Firm*—Smith, Gambrell & Russell, LLP

[57] ABSTRACT

The invention relates to new 1-[2-(substituted vinyl)]-3,4-dihydro-5$\underline{H}$-2,3-benzodiazepine derivatives, a process for the preparation thereof and pharmaceutical compositions comprising them. The new 1-[2-(substituted vinyl)]-3,4-dihidro-5H-2,3-benzodiazepine derivatives according to the invention correspond to the general formula (I),

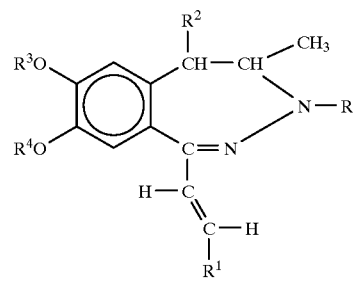

(I)

wherein the variables are hereinbelow defined: The new compounds according to the invention affect the central nervous system and can be used to advantage in the therapy.

8 Claims, No Drawings

1-[2-(SUBSTITUTED VINYL)]-3,4-DIHYDRO-4-DIHYDRO-5+e,UNS H+ee -2,3-BENZODIAZEPINE DERIVATIVES

This invention relates to new 1-[2-(substituted vinyl)]-3,4-dihydro-5H-2,3-benzodiazepine derivatives, a process for the preparation thereof, pharmaceutical compositions comprising the same, to the use of the said benzodiazepine derivatives for the treatment of diseases and for the preparation of pharmaceutical compositions suitable for the treatment of diseases.

So far 3,4-dihydro-5H-2,3-benzodiazepine derivatives containing a hydrogen atom or a methyl, phenyl, naphtyl, substituted phenyl, furyl or thienyl substituent at the 1 position of the basic molecule skeleton have been published (Hungarian patent specifications Nos. 168,760, 198,494 and 206,719, published Hungarian patent specification No. T/59684, Chem. Ber. 95, 2012 (1962); Helv. Chim. Acta 59, 2786 (1976); Synthesis 1973, 159 and 1977, 1; Acta Chim. Hung. 83, 115 (1974); Rec. Trav. Chim. 84, 661 (1965); J. Chem. Soc. Chem. Comm. 1972, 823; Il Farmaco. Ed. Sc. 40,942 (1985); Chem. Pharm. Bull. 30, 3764 (1982)].

The known 1-(4-aminophenyl)-4-methyl-7,8-methylenedioxy-5H-2,3-benzodiazepine (the compound referred to as GYKI-52466) is a non-NMDA-glutamic acid antagonist having spasmolytic and antiischemic activities, but the duration of its action is rather short, and this fact represents a disadvantage in the therapeutic applicability thereof.

The aim of the invention was to provide new 2,3-benzodiazepine derivatives comparable to the hitherto known benzodiazepines considering the effects on the central nervous system, but superior to them in view of the duration of the activity.

It has been found that the compounds according to the invention meet the above requirements.

According to an aspect of the present invention there are provided new 1-[2-(substituted vinyl)]-3,4-dihydro-5H-2,3-benzodiazepine derivatives of general formula (I),

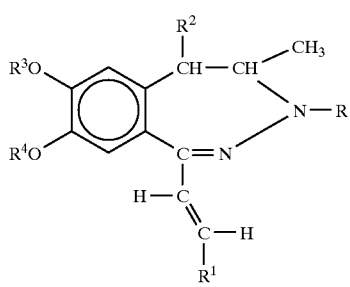

(I)

wherein
R represents hydrogen or $C_{1-4}$ alkanoyl,
$R^1$ stands for phenyl optionally carrying 1–3 identical or different substituent(s) selected from the group consisting of halogen, nitro, amino, $C_{1-4}$ alkylamino, di-($C_{1-4}$alkyl)-amino, $C_{1-4}$ alkanoylamino, $C_{1-4}$ alkyl, $C_{1-4}$ alkoxy, methylenedioxy and hydroxy; or naphtyl optionally carrying a substituent selected from the group consisting of hydroxy, $C_{1-4}$ alkyl and $C_{1-4}$ alkoxy;
$R^2$ stands for hydrogen or $C_{1-4}$ alkyl;
$R^3$ and $R^4$ are independently $C_{1-4}$ alkyl, or
$R^3$ and $R^4$ together form methylene, stereoisomers and their possible mixtures and pharmaceutically acceptable acid addition salts thereof.

Preferred representatives of the compounds of general formula (I) are those wherein R stands for $C_{1-4}$ alkanoyl, $R^1$ represents phenyl or naphtyl carrying a $C_{1-4}$ alkanoylamino or $C_{1-4}$ alkoxy substituent, $R^2$ denotes hydrogen or ethyl and $R^3$ and $R^4$ are independently $C_{1-4}$ alkyl.

Particularly preferred representatives of the compounds according to the invention are the following derivatives:
1-(4-acetylaminostyryl)-3-acetyl-4-methyl-7,8-dimethoxy-3,4-dihydro-5H-2,3-benzodiazepine,
1-[2-(1-naphtyl)-vinyl]-4-methyl-7,8-dimethoxy-3,4-dihydro-5H-2,3-benzodiazepine,
1-(2,3-dimethoxystyryl)-3-acetyl-4-methyl-7,8-dimethoxy-3,4-dihydro-5H-2,3-benzodiazepine,
stereoisomers and their possible mixtures and pharmaceutically acceptable acid addition salts thereof.

The term "lower" used throughout the specification and claims is intended to mean 1 to 4 carbon atom(s). The term "alkyl" refers to straight or branched chained ones having the given number of carbon atoms, such as methyl, ethyl, n-propyl, isopropyl etc. The term "alkoxy" relates to straight or branched chained alkyl ether groups, such as methoxy, ethoxy, isopropoxy etc. The term "alkanoylamino" relates to straight or branched chained aliphatic carboxylic acid amide groups (e.g. acetylamino, propanoyl-amino etc.). The term "halogen atom" encompasses all the four halogen atoms, such as fluorine, chlorine, iodine, and bromine.

Pharmaceutically acceptable acid addition salts of the compounds of general formula (I) can be formed with inorganic acids (e.g. hydrohalides, such as hydrochloric acid or hydrobromic acid, sulfuric, phosphoric or perhalo-acids, such as perchloric acid), organic carboxylic acids (e.g. fumaric, acetic, propionic, glycolic, maleic, hydrocymaleic, ascorbinic, citric, maleic, salicylic, lactic, cinnamic, benzoic, phenylacetic, p-aminobenzoic, p-hydroxybenzoic, p-aminosalicylic acid etc.), alkyl-sulfonic acids (e.g. methanesulfonic, ethanesulfonic acid), or arylsulfonic acids (e.g. p-toluenesulfonic, p-bromo-phenylsulfonic, naphtylsulfonic, sulfanilic acid).

According to a further aspect of the invention there is provided a process for the preparation of 1-[2-(substituted vinyl)]-3,4-dihydro-5H-2,3-benzodiazepines of general formula (I), which comprises
a) reducing a 5H-2,3-benzodiazepine of general formula (II),

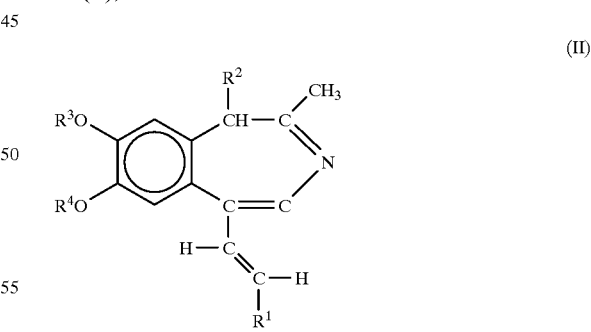

(II)

wherein $R^1$, $R^2$, $R^3$ and $R^4$ are as stated above, with a complex metal hydride and/or a borane complex, and optionally acylating the compound of general formula (I) thus obtained, wherein R stands for hydrogen and $R^1$, $R^2$, R3 and $R^4$ are as stated above, or
b) for the preparation of 1-[2-(substituted vinyl)]-3,4-dihydro-5H-2,3-benzodiazepines of general formula (I), wherein $R^1$ represents aminophenyl, ($C_{1-4}$ alkyl)-amino-phenyl, di-($C_{1-4}$ alkyl)-aminophenyl or ($C_{1-4}$ alkanoyl)-aminophenyl, and said groups optionally carry one or two identical or different substituent(s) selected from the group consisting of halogen, nitro, amino, methylenedioxy, hydroxy, $C_{1-4}$ alkyl and $C_{1-4}$ alkoxy, R, $R^2$, $R^3$ and $R^4$ are as stated above, reducing a compound of general formula (I), wherein $R^1$ represents nitrophenyl optionally carrying one or two identical or different substituent(s) selected from the group consisting of halogen, nitro, amino, methylenedioxy, hydroxy, $C_{1-4}$ alkyl and $C_{1-4}$ alkoxy, R, $R^2$, $R^3$ and $R^4$ are as stated above, with hydrazine hydrate in the presence of a catalyst, and optionally acylating or alkylating the thus-obtained amino compound, and, if desired, subjecting the thus-obtained compound of general formula (I) to resolution, or, if desired, converting the thus-obtained base of general formula (I) into a pharmaceutically acceptable acid addition salt thereof.

According to variant a) of the process according to the invention a 5$\underline{H}$-2,3-benzodiazepine of general formula (II) is reduced with a complex metal hydride and/or a borane complex, and the thus-obtained compound of general formula (I) containing hydrogen in the place of R is optionally acylated. For the selective reduction of the compounds of general formula (I) the following reducing agents may be applied: sodium borohydride, lithium aluminium hydride, borane and borane complexes. The reduction is preferably carried out in a solvent. For this purpose water, lower alcohols, lower carboxylic acids, solvents of ether type, aromatic hydrocarbons, chlorinated aliphatic hydrocarbons, pyridine or the mixtures thereof may be used. The solvents or solvent mixtures applicable in a given case depend on the applied reducing agent.

The reduction is carried out at a temperature between 0° C. and 100° C. using preferably 1.1 to 25 molar equivalent (s) of reducing agent.

According to a preferred embodiment of variant a) of the process according to the invention 1.5 to 2.0 equivalents of borotrifluoride etherate are added to a solution or suspension of the 5$\underline{H}$-2,3-benzodiazepine derivative of general formula (II) in dry dichloromethane at a temperature between 10° C. and 15° C., to the solution of the thus-obtained complex 1.1 equivalent of borane-tri-methylamine complex is added, and the reaction mixture is stirred at 25° C. for 0.5 to 4 hour(s). The organic phase is then treated with sodium carbonate, washed with water, dried, evaporated, the desired product is crystallized, filtered and optionally recrystallized from an appropriate solvent, e.g. from a lower alcohol, or suspended in an appropriate solvent.

According to a further preferred embodiment of variant a) of the process according to the invention the compound of general formula (II) is dissolved or suspended in anhydrous tetrahydrofurane, cooled to a temperature between 0° C. and 5° C., 1 molar equivalent of lithium aluminium hydride is added to it, and the reaction mixture is stirred at room temperature for 2 hours. The complex is then decomposed and the organic phase is evaporated. From the residue the desired 3,4-dihydro-5$\underline{H}$-2,3-benzodiazepine is obtained either by column chromatography or by crystallization, and, if desired, it is converted into the corresponding acyl derivative.

According to a further embodiment of variant a) or the process according to the invention the starting base of general formula (II) is dissolved or suspended in methanol, an excess of concentrated hydrochloric or acetic acid is added to it, and sodium borohydride is introduced to the thus-obtained hydrochloride or acetate. After working up the reaction mixture the desired 3,4-dihydro compound is obtained by crystallization, and, if desired, it is converted into the corresponding acyl derivative.

The acylation can be carried out by methods known in the literature, preferably with carboxylic acid halides or anhydrides.

According to variant b) of the process according to the invention 1-[2-(substituted vinyl)]-3,4-dihydro-5$\underline{H}$-2,3-benzodiazepine derivatives of general formula (I), wherein $R^1$ stands for aminophenyl, mono- or di-($C_{1-4}$ alkyl)-amino-phenyl optionally carrying one or two identical or different substituent(s) selected from the group consisting of halogen, nitro, methylenedioxy, hydroxy, $C_{1-4}$ alkyl and $C_{1-4}$ alkoxy, are produced by reducing the appropriate nitrophenyl derivative of general formula (I) with hydrazine hydrate in the presence of a catalyst, and optionally acylating or alkylating the thus-obtained amino compound. In order to reduce the nitro group a selective reducing method is to be applied, which does not saturate the vinyl group. So far no method has been provided in the literature for the reduction of such compounds. It has been found that hydrazine hydrate applied in the presence of a catalyst is suitable for the selective reduction of compounds of such type. So far hydrazine hydrate applied in the presence of a catalyst has been used only for the conversion of nitro compounds containing no other reducible group into the corresponding amino compounds [Chem. Rev. 65, 52, (1965); J. Am. Chem. Soc. 75, 4334 (1953); Chem. Lett. 1975, 259].

The reduction is preferably carried out in the presence of an organic solvent. Preferably the following solvents or the mixtures thereof can be applied: lower alcohols, dioxane, tetrahydrofurane, benzene, chloroform, dichloromethane, dimethylformamide, dimethyl sulfoxide and pyridine. It is preferable to carry out the reaction with an excess of 90–100% hydrazine hydrate. As catalyst preferably palladium on bone coal, platinum or Raney nickel can be applied. The reaction is carried out at a temperature between 0° C. and the boiling point of the solvent, preferably at a temperature between +10° C. and +100° C.

According to a preferred embodiment of process variant b) the 1-nitrostyryl-5$\underline{H}$-2,3-benzodiazepine derivative of general formula (II) is suspended in methanol and reacted with 2–4 equivalents, preferably 3 equivalents of 98–100% hydrazine hydrate in the presence of Raney nickel catalyst at room temperature for 1–2 hour(s). The crude product is separated from the reaction mixture by a method known per se. When the thus-obtained product is hardly soluble in methanol, that is a partial separation occurs, it is preferable to wash the catalyst several times with a solvent, wherein the product can be dissolved readily, such as chloroform. The crude product can be purified by recrystallization or trituration in a solvent. As solvent an alcohol, water or the mixtures thereof can be used.

The aminostyrylbenzodiazepine derivative of general formula (I) prepared as specified above is optionally alkylated or acylated.

The optional alkylation can be performed by methods known per se, preferably with an alkyl halide in an indifferent solvent, in the presence of an acid binding agent, at a temperature between room temperature and the boiling point of the solvent. As solvent preferably aliphatic alcohols, ketones, nitrives, tetrahydrofurane, dioxane, dimethylformamide or dimethyl sulfoxide can be used. As acid binding agent preferably an alkali carbonate, alkali hydrocarbonate or one or two equivalent(s) of a lower tert.amine may be used.

The aminostyrylbenzodiazepines of general formula (I) obtained as specified above are optionally acylated. The acylation is carried out by using one or two equivalent(s) of an acid halide or an acid anhydride. The reaction is preferably carried out in the presence of an acid binding agent, preferably in a lower aliphatic tert.amine or in pyridine. It is preferable to carry out the reaction in a solvent (e.g. in an aliphatic ketone, nitrile, tetrahydrofurane, dioxane, pyridine), but the reaction can also be performed without using any solvent, in an excess of the applied reagent.

The compounds of general formula (II) used as starting substances are new and can be prepared in a manner analogous to that described in Hungarian patent specification No. 195,788. The melting points of the new starting compounds are given below.

The new compounds of general formula (I) according to the invention possess valuable pharmaceutical properties, particularly central nervous activities. They bind with high affinity to the binding site specific for homophtalazines (2,3-benzodiazepines) [FEBS Letters 308 (2) 251–217 (1992)] suggesting that the compounds—assuming similar absorption and metabolism to those of 2,3-benzodiazepines—will exert considerable in vivo activities in the central nervous system. The $K_i$ values measured with 5 nM of $^3$H-girisopam [1-(3-chlorophenyl)-4-methyl-7,8-dimethoxy-5H-2,3-benzodiazepine] are shown in Table I. As reference compound girisopam was used, since it is also the standard ligand of this binding site. $K_i$ values were calculated using the following equation:

$$K_i = IC_{50} : 1 + \frac{[L]}{K_D}$$

wherein $K_D$ is the dissociation constant of the labelled ligand-receptor complex, [L] is the concentration of the labelled ligand and $IC_{50}$ is the half maximal inhibitory concentration of the test compound.

TABLE I

| Compound (No. of Example) | $K_i$ (mole/l) |
| --- | --- |
| 5 | 7.85 ± 0.51 · 10$^{-8}$ |
| 18 | 6.07 ± 2.15 · 10$^{-8}$ |
| 21 | 3.13 ± 0.74 · 10$^{-8}$ |
| 22 | 5.33 ± 1.20 · 10$^{-8}$ |
| Girisopam | 4.00 · 10$^{-8}$ |

The new compounds according to the invention considerably decrease the spontaneous motor activity (SMA) of mice after intraperitoneal or oral administration.

The SMA inhibiting effect and the acute toxicity data (dead/treated animals, shown in brackets) of the new compounds are provided in Table II.

The experiments were performed according to the method of S.Irwin [Psychopharm. 13, 222 (1968)].

TABLE II

| Compound | Dose (mg/kg) | | | | | |
| --- | --- | --- | --- | --- | --- | --- |
| (No. of Example) | p.o. 1000 | I.p. 300 | p.o. 300 | I.p. 100 | p.o. 100 | I.p. 30 |
| 1 | +−(0/5) | +−(0/5) | 0 | +− | 0 | 0 |
| 2 | ++ | ++ | + | +− | +− | 0 |
| 3 | ++(0/5) | +(0/5) | 0 | +− | 0 | 0 |
| 5 | +− | ++ | +− | +− | +− | +− |
| 20 | ++ | ++(1/5) | ++ | ++ | +− | +− |
| 22 | ++ | ++(1/5) | + | + | +− | +− |

TABLE II-continued

| Compound | Dose (mg/kg) | | | | | |
| --- | --- | --- | --- | --- | --- | --- |
| (No. of Example) | p.o. 1000 | I.p. 300 | p.o. 300 | I.p. 100 | p.o. 100 | I.p. 30 |
| 23 | +(0/5) | ++(0/5) | +− | +− | +− | +− |
| 26 | +−(0/5) | +−(0/5) | +− | +− | 0 | 0 |
| 27 | +− | +−(0/5) | +− | +− | +− | +− |
| 34 | + | + | + | + | + | 0 |
| 41 | +−(0/5) | +−(0/5) | +− | +− | +− | +− |
| Girisopam | | ++(0/6) | | +− | | 0 |

Symbols: ++ strong, + medium, +− mild decrease of SMA, 0: no effect

Contrary to the known molecules having similar chemical structure, the compounds according to the invention show a significant potentiation of the stereotypy induced by amphetamine suggesting a possible antidepressant activity. The potentiation of the stereotypy evoked by amphetamine was evaluated according to the scale of Constall and Naylor (Eur. J. Pharmacol. 18, 95, 1972). The results are shown in Table III.

TABLE III

| Compound (No. of Example) | Potentiation* % |
| --- | --- |
| 7 | 90.20 |
| 8 | 113.14 |
| 9 | 141.18 |
| 10 | 176.47 |
| 14 | 112.94 |
| 22 | 113.14 |
| 27 | 183.33 |
| 28 | 92.55 |
| 30 | 100 |
| 33 | 201.63 |
| 34 | 92.03 |
| 39 | 112.75 |
| 40 | 99.67 |

*10 mg/kg i.p. + amphetamine 3 mg/kg s.c.

The compounds of general formula (I) exert a moderate anticonvulsive effect, too. This latter was measured in mice applying the method of Goodmann et al.[J. Pharmacol. Exp. Ther. 106, 319, (1952)]. The convulsions evoked by 50 mg/kg i.v. of pentetrazole were inhibited by 30–40% and 50–55% after the i.p. administration of 30 mg/kg of the compounds of Examples 10., 11., 13., 19., 28., 35, 40., and Examples 34 and 38, respectively.

The effects of the compounds on the glutamatergic transmission were studied in hippocampal slices applying the method of Tarnawa et al. (Acta Physiol. Hung., 79, 163, 1992). 400 μm thick slices were prepared from rat brain and maintained in a chamber of interface type under simulated psychological conditions. The Schaffer collaterals were stimulated and field potentials were recorded from the pyramidal cells of the hippocampal CA1 region. The neurotransmitter involved in this process is glutamate acting mainly through AMPA receptors. The known AMPA antagonist, the compound referred to as GYKI-52466 concentration-dependently inhibits the CA1 field potentials. The results obtained are shown in Table IV.

TABLE IV

| Compound (No. of Example) | Concentration | Inhibition (%) 30 minutes after drug administration | Inhibition (%) 60 minutes after drug administration | Inhibition (%) after 30 minutes wash-out |
|---|---|---|---|---|
| GYKI-52466 | 50 µM | 94.5 ± 2.07 | 100 ± 0 | 84.6 ± 7.37* |
| 39 | 50 µM | 85.3 ± 15.09 | 100 ± 0 | 97.5 ± 0.98 |
| 40 | 50 µM | 14.8 ± 7.10 | 25.8 ± 3.04 | 35.4 ± 2.67 |
| 41 | 50 µM | 79.5 ± 10.10 | 100 ± 0 | 98.6 ± 2.67 |
| 21 | 50 µM | 16.1 ± 13.4 | 33.7 ± 7.60 | 61.1 ± 4.56 |
| 22 | 50 µM | 4.7 ± 0.84 | 37.0 ± 9.19 | 74.3 ± 11.53 |

*$p < 0.05$ compared to the 60 minutes value

The compounds of Examples 39 and 41 showed at least equal efficacy to the molecule GYKI-52466. In the case of the latter compound, however, the inhibition observed after a wash-out lasting for 30 minutes was significantly smaller than that observed after the preceding incubation period lasting for 60 minutes, while in the case of the compounds of Examples 39 and 41 a wash-out lasting for 30 minutes was not able to diminish the effect. This means that the duration of action of the latter compounds surpass that of GYKI-52466. In the case of the further three test substance the inhibition observed after the wash-out period was even higher than that observed at the end of the preceeding incubation period.

The inhibition of the hippocampal field potentials supports the possible antiischemic and neuroprotective therapeutical use of the new compounds [Le Peillet et al.: Eur. J. Neurosci., 4 (suppl.), 1068, 1991]. According to our results the duration of action of the new compounds exceeds those of the known molecules having similar effect.

According to a further aspect of the present invention there are provided pharmaceutical compositions comprising as active ingredient a compound of general formula (I) or a pharmaceutically acceptable acid addition salt thereof in admixture with suitable inert solid or liquid pharmaceutical carriers.

The pharmaceutical compositions of the present invention can be prepared by methods known per se by admixing the active ingredient with suitable inert solid or liquid carriers and bringing the mixture to galenic form.

The pharmaceutical compositions of the present invention may be suitable for oral (e.g. tablet, pill, coated pill, dragée, solid or soft gelatin capsule, solution, emulsion or suspension), parenteral (e.g. injection solution) or rectal (e.g. suppository) administration.

As carrier for the preparation of tablets, coated tablets, dragées and solid gelatin capsules e.g. lactose, corn starch, potato starch, talc, magnesium carbonate, magnesium stearate, calcium carbonate, stearic acid or the salts thereof, etc. can be used. As carrier for the soft gelatin capsules e.g., vegtable oils, fats, waxes or polyols of suitable consistency can be used. As carriers for the solutions and syrups e.g. water, polyols (polyethylene glycol), saccharose or glucose can be used. The injection solutions can comprise e.g. water, alcohols, polyols, glycerol or vegetable oils as carrier. The suppositories can be prepared with the aid of e.g. oils, waxes, fats or polyols of suitable consistency.

In addition, the pharmaceutical formulations may comprise auxiliaries usually applied in pharmaceutical industry, e.g. wetting, sweetening agents, aroma substances, salts causing the change of osmotic pressure, buffers etc. The pharmaceutical formulations may further comprise other active ingredients, too.

The daily dose of the compounds of general formula (I) can vary within wide ranges depending on several factors, e.g. on the activity of the active ingredient, the patient's condition and age, the severity of the disease etc. The preferred oral dose is generally 0.1 to 500 mg/day. It has to be stressed that the above dose is only of informative character and the administered dose must always be determined by the physician therapeutist.

According to a further aspect of the present invention there is provided the use of the compounds of genreal formula (I) or pharmaceutically acceptable acid addition salts thereof for the preparation of pharmaceutical compositions affecting particularly the central nervous system.

According to a still further aspect of the present invention there is provided a method for the treatment of central nervous system disorders, which comprises administering to a patient an effective amount of a compound of general formula (I) or a pharmaceutically acceptable acid addition salt thereof.

Further details of the present invention are to be found in the following Examples without limiting the scope of protection to the said Examples.

The new compounds according to the invention were identified by elemental analysis, IR, $^1$H-NMR and mass spectroscopy. The protons of the olefin bond are exclusively of trans-position.

EXAMPLE 1

1-(3,4-Dimethoxystyryl)-4-methyl-7,8-methylenedioxy-3,4-dihydro-5H-2,3-benzodiazepine To a solution of 2.04 g (5.6 mmoles) 1-(3,4-dimethoxystyryl)-4-methyl-7,8-methylenedioxy-5H-2,3-benzodiazepine in 40 ml of anhydrous dichloromethane 1.0 ml (8.4 mmoles) of borotrifluoride etherate is added under cooling with tap water, and 0.45 g (6.16 mmoles) of borane trimethylamine complex is added to it. The reaction mixture is stirred at 25° C. for 0.5 hour, and then 30 ml of 10% aqueous sodium carbonate solution are dropped to it under cooling with tap water, and the mixture is stirred further for 1 hour. The organic phase is separated, washed four times with 30 ml each of distilled water, dried and evaporated. The crystalline residue is suspended in 10 ml of ethanol, filtered, washed three times with 1 ml each of ethanol and dried at a temperature between 80° C. and 100° C. Thus 1.76 g of the desired product is obtained. M.p.: 166–168° C.

In order to purify the crude product. It is boiled in 10 ml of ethanol, cooled, filtered, washed three times with 1 ml each of ethanol and dried. Thus 1.69 g (82.4%) of the desired product is obtained. M.p.: 168–170° C.

Further compounds of general formula (I), wherein R represents hydrogen, have also been prepared according to the method of Example 1, which are summarized in the following Table V.

TABLE V

| Compound (No. of Example) | $R^1$ | $R^2$ | $R^3$ | $R^4$ | $BF_3$ etherate mole | M.p. (° C.) | Cryst. | Yield |
|---|---|---|---|---|---|---|---|---|
| 2 | 3-chlorophenyl | H | Me | Me | 1.5 | 105–107 | 80% EtOH | 61.0 |
| 3 | 3,4-methylenedioxyphenyl | H | Me | Me | 1.5 | 163–164 | EtOH | 76.5 |
| 4 | 4-hydroxyphenyl | H | Me | Me | 1.5 | 160–162 | 50% EtOH | 43.0 |
| 5 | 3-ethoxy-4-hydroxyphenyl | H | Me | Me | 1.5 | 138–139 | 50% EtOH | 50.0 |
| 6 | 2,4,6-trimethoxyphenyl | H | Me | Me | 1.5 | 144–146 | EtOH | 80.0 |
| 7 | 4-dimethylaminophenyl | H | Me | Me | 2 | 145–147 | 50% EtOH | 76.6 |
| 8 | 3,4-methylenedioxyphenyl | H | —CH$_2$— | | 1.5 | 181–183 | EtOH | 86.0 |
| 9 | 4-dimethylaminophenyl | H | —CH$_2$— | | 2 | 156–158 | EtOH | 76.2 |
| 10 | 4-dimethylaminophenyl | H | Et | Et | 2 | 149–151 | EtOH | 78.6 |
| 11 | 3-hydroxyphenyl | H | Me | Me | 1.5 | 106–108 | EtOH | 46.0 |
| 12 | phenyl | H | Me | Me | 1.5 | 120–121 | EtOH | 65.0 |
| 13 | 3-isopropyl-4-methoxyphenyl | H | CH$_2$— | | 1.5 | 149–151 | EtOH | 77.7 |
| 14 | 2-bromophenyl | H | Me | Me | 1.5 | 130–131 | EtOH | 50.0 |
| 15 | 3,4-dimethoxyphenyl | CH$_3$CH$_2$ | Me | Me | 1.75 | 157–158 | EtOH | 59.0 |

EXAMPLE 16

1-(2,3-Dimethoxystyryl)-4-methyl-7,8-methylenedioxy-3,4-dihydro-5$\underline{H}$-2,3-benzodiazepine hydrochloride 1.5 g (4.12 mmoles) of 1-(2,3-dimethoxystyryl)-4-methyl-7,8-methylenedioxy-5$\underline{H}$-2,3-benzodiazepine is reduced as specified in Example 1, the evaporation residue is dissolved in ethyl acetate and 10 ml of 10% by mass of ethyl acetate saturated with gaseous hydrogen chloride are added to the solution. The separated product is filtered, washed three times with 5 ml each of ethyl acetate and dried at a temperature between 80° C. and 100° C. Thus 0.76 g (45.8%) of the desired product is obtained. M.p.: 193–195° C. (decomp)

EXAMPLE 17

1-(2,4-Dimethoxystyryl)-4-methyl-7,8-methylenedioxy-3,4-dihydro-5$\underline{H}$-2,3-benzodiazepine A suspension of 1,1 g (3.0 mmoles) of 1-(2,4-dimethoxystyryl)-4-methyl-7,8-methylenedioxy-5$\underline{H}$-2,3-benzodiazepine in 15 ml of anhydrous tetrahydrofurane is cooled to a temperature between 0° C. and 5° C., and 0.114 g (3.0 mmoles) of lithium aluminium hydride is added to it. The reaction mixture is stirred at 25° C. for 2 hours, cooled again to a temperature between 0° C. and 5° C. and decomposed with 0.36 ml of 10% aqueous potassium sodium tartrate solution. Then it is stirred further for 1 hour at 25° C., the precipitate is filtered off, the filtrate is dried and evaporated under reduced pressure. The crude end-product is recrystallized from 10 ml of ethanol, filtered, washed three times with 1 ml each of ethanol and dried at a temperature between 80° C. and 100° C. Thus 0.84 g (76.0%) of the desired product is obtained.

M.p.: 176–178° C.

EXAMPLE 18

1-(2,4-Dimethoxystyryl)-4-methyl-7,8-dimethoxy-3,4-dihydro-5$\underline{H}$-2,3-benzodiazepine On starting from 1-(2,4-dimethoxystyryl)-4-methyl-7,8-dimethoxy-5$\underline{H}$-2,3-benzodiazepine the procedure specified in Example 17 is followed, with the difference that the crude product obtained after the evaporation is purified by column chromatography [adsorbent: Kieselgel 60, particle size: 0.063–2 mm; eluent: benzene-methanol-cc. NH$_4$OH (8:2:0.1)]. The desired compound is obtained in crystalline form upon evaporating the fractions. Yield: 53%.

M.p.: 118–120° C.

EXAMPLE 19

1-(2,4-Dimethoxystyryl)-3-acetyl-4-methyl-7,8-methylenedioxy-3,4-dihydro-5$\underline{H}$-2,3-benzodiazepine The crude product obtained when evaporating the compound of Example 17 is dissolved in 7 ml of chloroform, 0.7 ml of acetic anhydride is added to it and the mixture is boiled for 2 hours. Then it is cooled to room temperature, 10 ml of water are added to it, and the mixture is adjusted to pH=7–8 by the addition of sodium hydrogen carbonate. The organic phase is separated, the aqueous phase is extracted three times with 5 ml each of chloroform, the extracts are combined and washed twice with 10 ml each of distilled water, dried and evaporated under reduced pressure. The evaporation residue is recrystallized from ethanol. Thus 0.8 g (65%) of the desired product is obtained.

M.p.: 185–187° C.

The compounds of the following Examples 20 to 23 can be prepared according to the method of Example 19.

EXAMPLE 20
1-Styryl-3-acetyl-4-methyl-7,8-dimethoxy-3,4-dihydro-5H-2,3-benzodiazepine Yield: 50.0%. M.p.: 118–120° C. (EtOH).

EXAMPLE 21
1-(2,4-Dimethoxystyryl)-3-acetyl-4-methyl-7,8-dimethoxy-3,4-dihydro-5H-2,3-benzodiazepine Yield: 56.0%. M.p.: 85–87° C. (EtOH).

EXAMPLE 22
1-(2,3-Dimethoxystyryl)-3-acetyl-4-methyl-7,8-dimethoxy-3,4-dihydro-5H-2,3-benzodiazepine Yield: 58.0%. M.p.: 72–74° C. (EtOH).

EXAMPLE 23
1-(2,3-Dimethoxystyryl)-3-acetyl-4-methyl-7,8-methylenedioxy-3,4-dihydro-5H-2,3-benzodiazepine Yield: 60.0%. M.p.: 125–128° C. (EtOH).

EXAMPLE 24
1-(4-Nitrostyryl)-4-methyl-7,8-methylenedioxy-3,4-dihydro-5H-2,3-benzodiazepine To a suspension of 3.6 g (10.3 mmoles) of 1-(4-nitrostyryl)-4-methyl-7,8-methylenedioxy-5H-2,3-benzo-diazepine in 130 ml of methanol 17.7 ml (0.218 mole) of concentrated hydrogen chloride are added, under stirring. To the solution obtained in a few minutes 9.8 g (0.259 mole) of sodium borohydride are added in portions, within 30 minutes, and the mixture is stirred further for 30 minutes. Then 150 ml of distilled water is dropped to the orange suspension, the crude product is filtered off, washed four times with 20 ml each of distilled water and dried at a temperature between 80° C. and 100° C. Thus 3.37 g of the desired product are obtained. In order to purify the crude product it is boiled with 17 ml of ethanol, cooled, filtered, washed and dried. Thus 2.67 g (73.8%) of the desired compound are obtained.

M.p.: 175–177° C. (decomp.).

The compounds of the following Examples 25 to 29 can be prepared according to the method of Example 24.

EXAMPLE 25
1-(4-Nitrostyryl)-4-methyl-7,8-dimethoxy-3,4-dihydro-5H-2,3-benzodiazepine Yield: 65,0%. M.p.: 173–175° C. (decomp.) (EtOH).

EXAMPLE 26
1-(4-Nitrostyryl)-4-methyl-5-ethyl-7,8-dimethoxy-3,4-dihydro-5H-2,3-benzodiazepine Yield: 64.5%. M.p.: 168–169° C. (decomp.) (EtOH).

EXAMPLE 27
1-Styryl-4-methyl-7,8-methylenedioxy-3,4-dihydro-5H-2,3-benzodiazepine One proceeds as specified in Example 24, with the difference that after the addition of the sodium borohydride and the completion of the reaction the mixture is evaporated, and the crude product solidified with water is recrystallized from ethanol.

Yield: 40%. M.p.: 153–154° C.

EXAMPLE 28
1-(3,4-Dichlorostyryl)-4-methyl-7,8-dimethoxy-3,4-dihydro-5H-2,3-benzodiazepine One proceeds as specified in Example 24, and the reaction mixture is worked up according to Example 27.

Yield: 54.0% M.p.: 132–133° C. (EtOH).

EXAMPLE 29
1-(3-Chlorostyryl)-4-methyl-7,8-methylenedioxy-3,4-dihydro-5H-2,3-benzodiazepine One proceeds as specified in Example 24 and the reaction mixture is then worked up according to Example 27.

Yield: 40.0%. M.p. 114–117° C. (EtOH).

EXAMPLE 30
1-(4-Nitrostyryl)-3-acetyl-4-methyl-7,8-dimethoxy-3,4-dihydro-5H-2,3-benzodiazepine 2.6 g (7.07 mmoles) of the compound prepared according to Example 25 are stirred with 13 ml of acetic anhydride at 25° C. for 1 hour, 50 ml of distilled water are added to it and the mixture is stirred further for 1 hour. The separated yellow precipitate is filtered off, washed three times with 15 ml each of distilled water and dried at a temperature between 80° C. and 100° C. Thus 2.68 g of crude product are obtained, which is recrystallized from 13 ml of hot ethanol. Thus 2.62 g (90.6%) of the desired product are obtained in pure form. M.p.: 182–184° C.

The compounds of the following Examples 31 and 32 are prepared according to the method specified in Example 30.

EXAMPLE 31
1-(4-Nitrostyryl)-3-acetyl-4-methyl-7,8-methylenedioxy-3,4-dihydro-5H-2,3-benzodiazepine Yield: 91.0%. M.p.: 188–190° C. (EtOH).

EXAMPLE 32
1-(4-Nitrostyryl)-3-acetyl-4-methyl-5-ethyl-7,8-dimethoxy-3,4-dihydro-5H-2,3-benzodiazepine Yield: 88% M.p.: 184–185° C.

EXAMPLE 33
1-(4-Aminostyryl)-4-methyl-7,8-dimethoxy-3,4-dihydro-5H-2,3-benzodiazepine 6.95 g (18.9 mmoles) of 1-(4-nitrostyryl)-4-methyl-7,8-dimethoxy-3,4-dihydro-5H-2,3-benzodiazepine prepared according to Example 25 are suspended in 170 ml of methanol, 0.7 g of dry (corresponding to about 1.4 g of wet) Raney nickel catalyst and 3.3 ml (66 mmoles) of 100% hydrazine hydrate are added to it and the reaction mixture is stirred for 1 hour. A solution is obtained, and in the beginning the inner temperature rises to 40–45° C. The catalyst is filtered off, washed three times with 15 ml each of methanol, the filtrate is evaporated in vacuo, the crude product is conveyed to a filter with 80 ml of water, washed three times with 15 ml each of water and dried. Thus 5.46 g of product are obtained. In order to purify the crude product it is recrystallized from 25 ml of 50% ethanol. Thus 4.21 g (66.0%) of the desired product are obtained. M.p.: 152–154° C.

The compounds of the following Examples 34 to 38 can be prepared according to the method of Example 33.

EXAMPLE 34
1-(4-Aminostyryl)-4-methyl-7,8-methylenedioxy-3,4-dihydro-5H-2,3-benzodiazepine Yield: 80.0%. M.p.: 159–161° C. (50% EtOH).

EXAMPLE 35
1-(4-Aminostyryl)-4-methyl-5-ethyl-7,8-dimethoxy-3,4-dihydro-5H-2,3-benzodiazepine Yield: 75.5%. M.p.: 155–158° C. (50% EtOH).

EXAMPLE 36
1-(4-Aminostyryl)-3-acetyl-4-methyl-7,8-dimethoxy-3,4-dihydro-5H-2,3-benzodiazepine One proceeds as specified in Example 33, with the difference that owing to the hard solubilities of the starting compound and the end-product a 2:1 mixture of dichloromethane and methanol is used as solvent.

Yield: 81.4%, m.p.: 253–255° C. (decomp.) (EtOH).

EXAMPLE 37
1-(4-Aminostyryl)-3-acetyl-4-methyl-7,8-methylenedioxy-3,4-dihydro-5H-2,3-benzodiazepine Yield: 68.9% M.p.: 233–234° C. (decomp.) (EtOH).

EXAMPLE 38
1-(4-Aminostyryl)-3-acetyl-4-methyl-5-ethyl-7,8-dimethoxy-3,4-dihydro-5H-2,3-benzodiazepine Yield: 77.1% M.p.: 104–106° C. (EtOH)

EXAMPLE 39
1-(4-Acetylaminostyryl)-3-acetyl-4-methyl-7,8-dimethoxy-3,4-dihydro-5H-2,3-benzodiazepine 1.2 g (3.56,mmoles) of 1-(4-aminostyryl)-4-methyl-7,8-dimethoxy-3,4-dihydro-5H-2,3-benzodiazepine prepared according to Example 33 is suspended in 6 ml of acetic anhydride. The suspension is stirred for 1 hour at room temperature. In the meantime the starting compound gets dissolved, the end-product begins to separate and the reaction mixture gets thick. The separated product is filtered off, washed three times with 15 ml each of diethyl ether and dried at a temperature between 80° C. and 100° C. Thus 1.07 g (71.3%) of the desired compound is obtained.
M.p.: 243–246° C. (decomp.)

On starting from the compound of Example 36 and proceeding as specified in Example 39 the desired compound is obtained in a yield of 78%.

The compounds of the following Examples 40 and 41 can be prepared according to the method specified in Example 39.

EXAMPLE 40
1-(4-Acetylaminostyryl)-3-acetyl-4-methyl-7,8-methylenedioxy-3,4-dihydro-5H-2,3-benzodiazepine Yield: 91.0%. M.p.: 252–255° C. (decomp.)

EXAMPLE 41
1-(4-Acetylaminostyryl)-3-acetyl-4-methyl-5-ethyl-7,8-methylenedioxy-3,4-dihydro-5H-2,3-benzodiazepine Yield: 73.5%. M.p.: 137–140° C. (EtOH).

EXAMPLE 42
1-[2-(1-Naphtyl)-vinyl]-4-methyl-7,8-dimethoxy-3,4-dihydro-5H-2,3-benzodiazepine To a solution of 5.35 g (14.3 mmoles) of 1-[2-(1-naphtyl)-vinyl]-4-methyl-7,8-dimethoxy-5H-2,3-benzodiazepine in 30 ml of glacial acetic acid a solution of 1.76 g (46.3 mmoles) of sodium borohydride in 10 ml of water is dropped at 50° C., under stirring, and the reaction mixture is stirred further for 2 hours. The product is then stirred with 250 ml of water, made alkaline with ammonium hydroxide solution, the separated yellow precipitate is filtered, washed with water and recrystallized from isopropanol. Thus 3.75 g (70.5%) of the desired compound are obtained.
M.p.: 148–152° C.

The new starting compounds used for the preparation of the compounds of the above Examples are summarized in Table VI.

TABLE VI

| Compound (No. of Example) | R1 | R2 | R3 | R4 | M.p. (° C.) |
|---|---|---|---|---|---|
| 1. | 3,4-dimethoxyphenyl | H | —CH$_2$— | | 206–208 |
| 2. | 3-chlorophenyl | H | Me | Me | 178–180 |
| 3. | 3,4-methylenedioxyphenyl | H | Me | Me | 158–160 |
| 4. | 4-hydroxyphenyl | H | Me | Me | 212–213 |
| 5. | 3-ethoxy-4-hydroxyphenyl | H | Me | Me | 120–122 |
| 6. | 2,4,6-trimethoxyphenyl | H | Me | Me | 191–193 |
| 7. | 4-dimethylaminophenyt | H | Me | Me | 170–172 |
| 8. | 3,4-methylenedioxyphenyl | H | —CH$_2$— | | 223–225 |
| 9. | 4-dimethylaminophenyl | H | —CH$_2$— | | 219–222 |
| 10. | 4-dimethylaminophenyl | H | Et | Et | 158–160 |
| 11. | 3-hydroxyphenyl | H | Me | Me | 220–221 |
| 12. | phenyl | H | Me | Me | 143–145 |
| 13. | 3-isopropyl-4-methoxyphenyl | H | —CH$_2$— | | 155–157 |
| 14. | 2-bromophenyl | H | Me | Me | 176–178 |
| 15. | 3,4-dimethoxyphenyl | Et | Me | Me | 158–160 |
| 16. | 2,3-dimethoxyphenyl | H | —CH$_2$— | | 149–150 |
| 17. | 2,4-dimethoxyphenyl | H | —CH$_2$— | | 210–212 |
| 18. | 2,4-dimethoxyphenyl | H | Me | Me | 151–153 |
| 24. | 4-nitrophenyl | H | —CH$_2$— | | 227–228 |
| 25. | 4-nitrophenyl | H | Me | Me | 224–226 |
| 26. | 4-nitrophenyl | Et | Me | Me | 218–220 |
| 27. | phenyl | H | —CH$_2$— | | 153–154 |
| 28. | 3,4-dichlorophenyl | H | Me | Me | 168–169 |
| 29. | 3-chlorophenyl | H | —CH$_2$— | | 135–137 |
| 42. | 1-naphtyl | H | Me | Me | 148–152 |

What we claim is:

1. 1-3,4-dihydro-5H-2,3-benzodiazepine derivatives of formula (I),

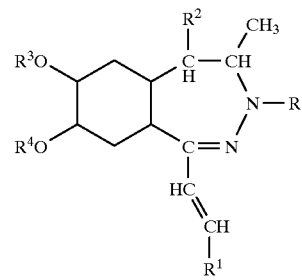

R represents hydrogen or C$_{1-4}$ alkanoyl,

R$^1$ stands for phenyl optionally carrying 1–3 identical or different substituent(s) selected from the group consisting of halogen, nitro, amino, C$_{1-4}$ alkylamino, di-(C$_{1-4}$ alkyl)-amino, C$_{1-4}$ alkanoylamino, C$_{1-4}$ alkyl, C$_{1-4}$ alkoxy, methylenedioxy and hydroxy; or naphtyl optionally carrying a substituent selected from the group consisting of hydroxy, C$_{1-4}$ alkyl and C$_{1-4}$ alkoxy;

R$^2$ stands for hydrogen or C$_{1-4}$ alkyl;

R$^3$ and R$^4$ are independently C$_{1-4}$ alkyl, or

R$^3$ and R$^4$ together form methylene, stereoisomers or mixtures of stereoisomers or pharmaceutically acceptable acid addition salts thereof.

2. Compounds of formula (I) as defined in claim 1, wherein R represents C$_{1-4}$ alkanoyl, R$^1$ stands for phenyl or naphtyl carrying a C$_{1-4}$ alkanoylamino or C$_{1-4}$ alkoxy substituent, $R^2$ stands for hydrogen or ethyl and $R^3$ and $R^4$ are independently $C_{1-4}$ alkyl.

3. The following compounds of formula (I) as defined in claim 1:
1-(4-acetylaminostyryl)-3-acetyl-4-methyl-7,8-dimethoxy-3,4-dihydro-5H-2,3-benzodiazepine, 1[2-(1-naphtyl)-vinyl]-4-methyl-7,8-dimethoxy-3,4-dihydro-5H-2,3-benzodiazepine, 1-(2,3-dimethoxystyryl)-3-acetyl-4-methyl-7,8-dimethoxy-3,4-dihydro-5H-2,3-benzodiazepine, stereoisomers or mixtures of stereoisomers or pharmaceutically acceptable acid addition salts thereof.

4. A pharmaceutical composition comprising as active ingredient one or more compounds as defined in claim 1, a stereoisomer or a pharmaceutically acceptable acid addition salt thereof, in admixture with a suitable inert solid or liquid pharmaceutical carrier.

5. A method for the treatment of anxiety which comprises administering to a patient in need thereof an effective amount of a compound according to claim 1.

6. A method for the treatment of anxiety which comprises administering to a patient in need thereof an effective amount of a compound according to claim 2.

7. A method for the treatment of anxiety which comprises administering to a patient in need thereof an effective amount of a compound according to claim 3.

8. A pharmaceutical composition comprising as active ingredient a member selected from the group consisting of 1-(4-acetylaminostyryl)-3-acetyl-4-methyl-7,8-dimethoxy-3,4-dihydro-5H-2,3-benzodiazepine, 1-[2-(1-naphtyl)-vinyl]-4-methyl-7,8-dimethoxy- 3,4-dihydro-5H-2,3-benzodiazepine, 1-(2,3-dimethoxystyryl)-3-acetyl-4-methyl-7,8-dimethoxy-3,4-dihydro-5H-2,3-benzodiazepine, or combinations thereof or pharmaceutically acceptable acid addition salts thereof and a pharmaceutically suitable carrier.

* * * * *